(12) United States Patent
Kobayashi et al.

(10) Patent No.: US 6,415,236 B2
(45) Date of Patent: Jul. 2, 2002

(54) APPARATUS FOR DETERMINING CONCENTRATIONS OF HEMOGLOBINS

(75) Inventors: Naoki Kobayashi; Michio Kanemoto; Takashi Usuda; Teiji Ukawa, all of Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 30 days.

(21) Appl. No.: 09/725,865

(22) Filed: Nov. 30, 2000

(30) Foreign Application Priority Data

Nov. 30, 1999 (JP) .......................... 11-339605
Sep. 21, 2000 (JP) ....................... 2000-286927

(51) Int. Cl.$^7$ .......................... A61B 5/00; G06F 159/00
(52) U.S. Cl. ............................. 702/30; 702/31; 702/19; 600/322
(58) Field of Search ............................. 702/19, 30, 31, 702/179; 600/322, 323; 356/39, 40, 41

(56) References Cited

U.S. PATENT DOCUMENTS

| | | | |
|---|---|---|---|
| 5,413,100 A | 5/1995 | Barthelemy et al. | 128/633 |
| 5,503,148 A | 4/1996 | Pologe et al. | 128/633 |
| 5,720,284 A | 2/1998 | Aoyagi et al. | 128/633 |
| 5,830,137 A | 11/1998 | Scharf | 600/323 |
| 5,842,979 A | 12/1998 | Jarman | 600/322 |
| 5,983,122 A | 11/1999 | Jarman et al. | 600/323 |

FOREIGN PATENT DOCUMENTS

| | | | |
|---|---|---|---|
| JP | 53-26437 | 8/1978 | A61B/5/00 |
| JP | 5-228129 | 9/1993 | A61B/5/14 |
| JP | 5-88609 | 12/1993 | A61B/5/14 |
| JP | 8-322822 | 12/1996 | A61B/5/14 |

OTHER PUBLICATIONS

The 22$^{nd}$ Japan intoxixation academic conference, with Abstract in English No date.
Annals of Biomedical Engineering; vol. 28 Supplement 1 No date.
Chest 2000; The Cardiopulmonary and Critical Care Journal No date.
The Japanese Journal of Toxicology; vol. 13 No. 4; 2000 No date.

*Primary Examiner*—Kamini Shah
(74) *Attorney, Agent, or Firm*—Sughrue Mion, PLLC

(57) ABSTRACT

An apparatus for determining concentrations of hemoglobins additionally uses a light source 3 which emits light of a third wavelength in an orangy red wavelength region of 590 to 660 nm. The apparatus includes light receiving means 6 for receiving lights that are emitted by the light sources and transmitted through or reflected by a living tissue, attenuation ratio processing means 15 for processing attenuation ratios Φ on the wavelengths based on variations of signals associated with the wavelengths output from the light receiving means, which variations are caused by a pulsation of blood, and concentration ratio processing means 16 for processing concentration ratios of at least oxyhemoglobin, deoxyhemoglobin and carboxyhemoglobin based on the output signals from the attenuation ratio processing means. The apparatus thus constructed can properly measure carboxyhemoglobin COHb, and present its concentration display and an alarm display in a simple manner, which is clinically effective.

17 Claims, 8 Drawing Sheets

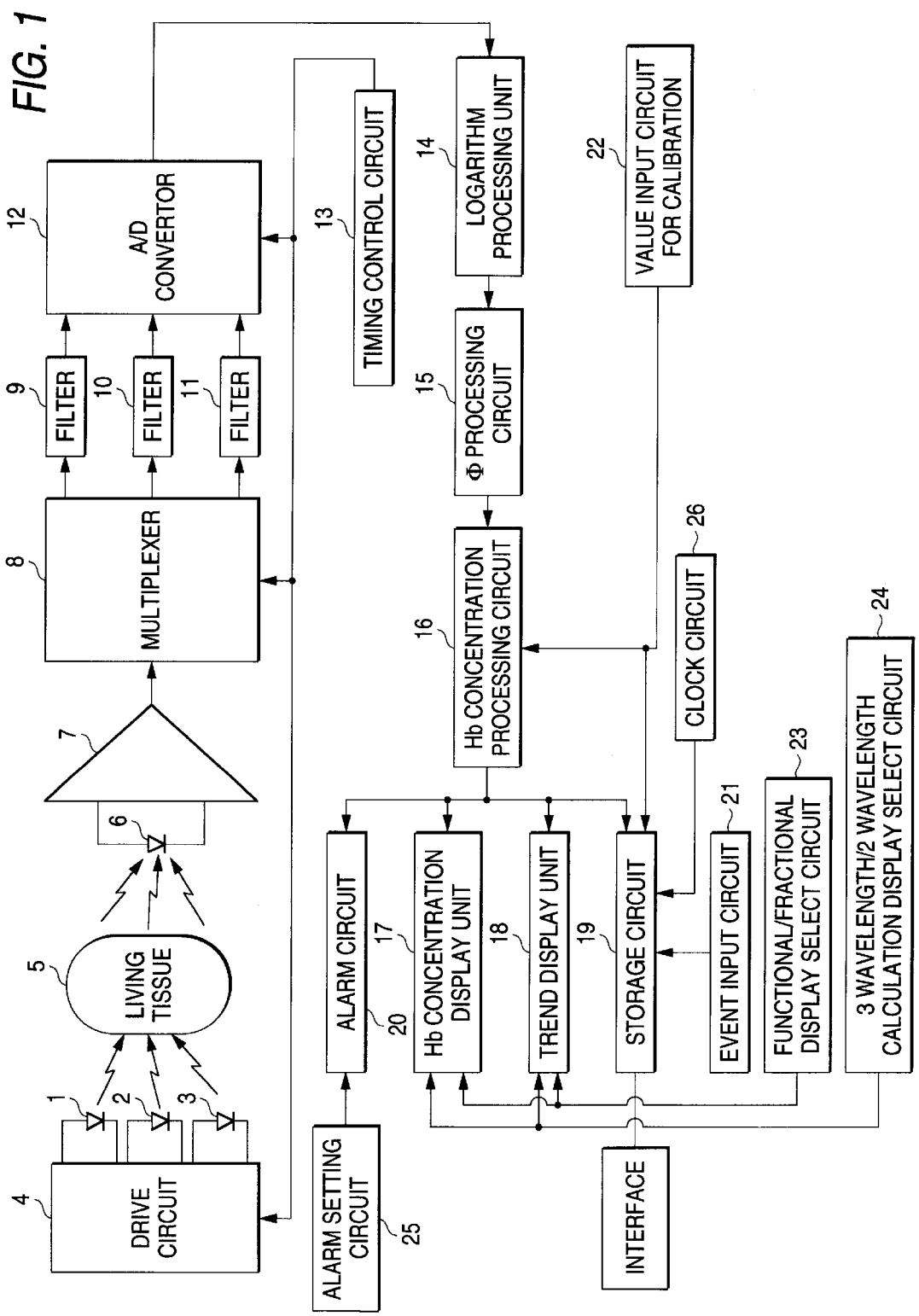

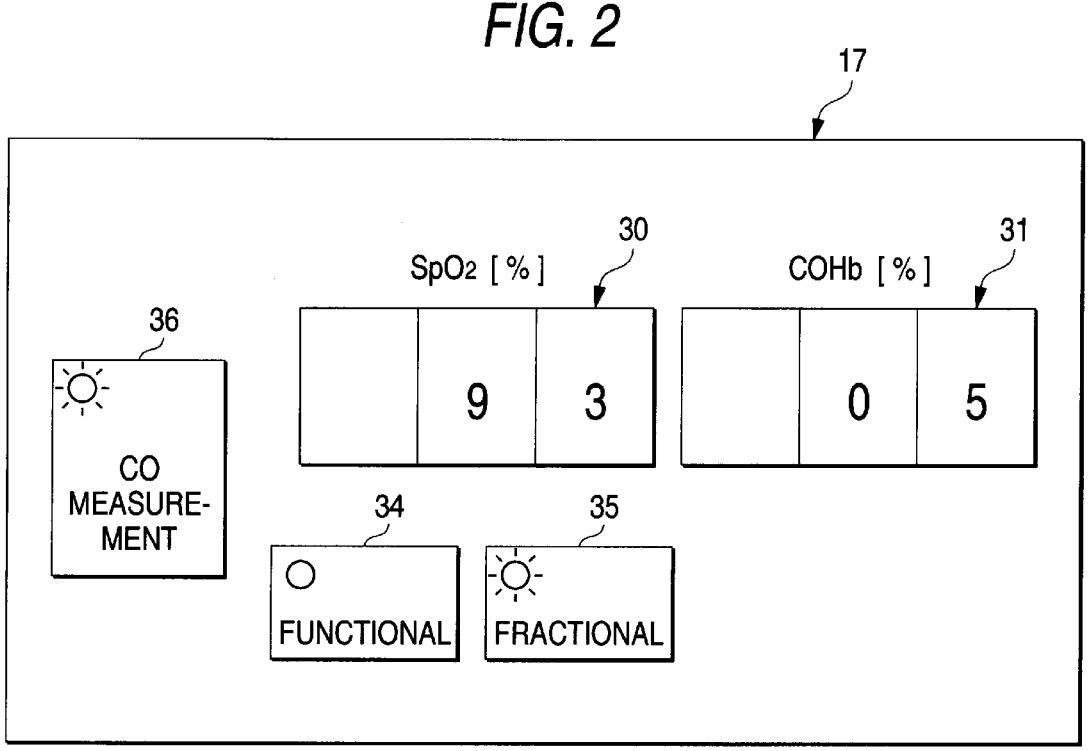
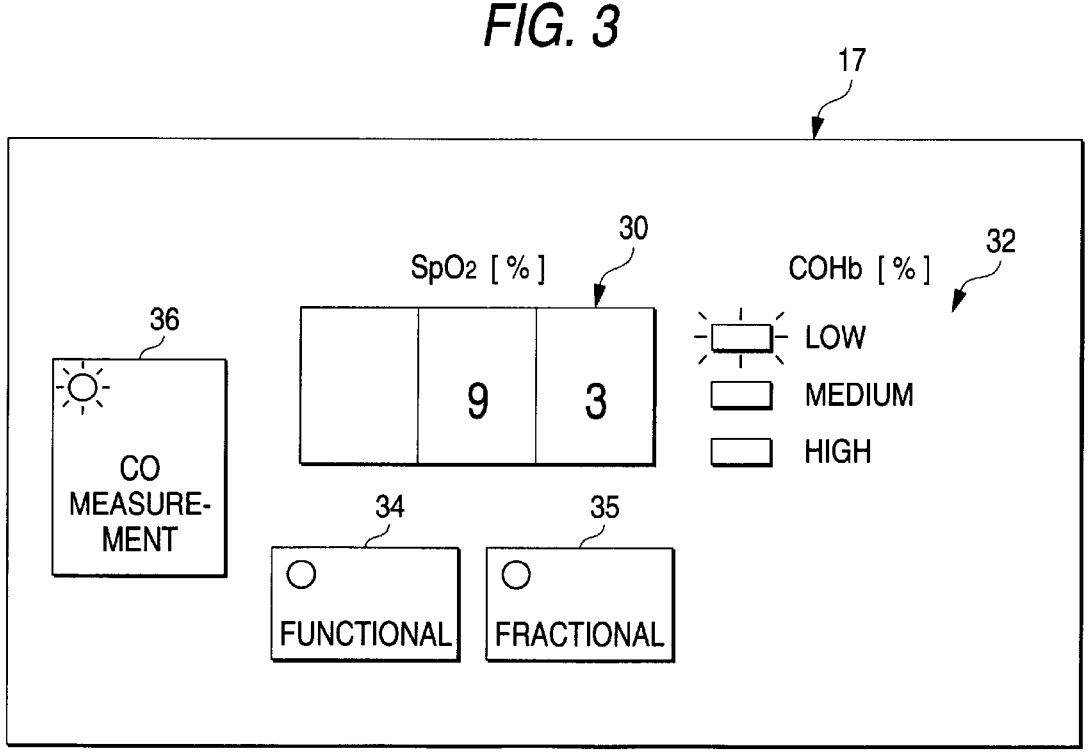

APPARATUS FOR DETERMINING CONCENTRATIONS OF HEMOGLOBINS

BACKGROUND OF INVENTION

1. Field of the Invention

The present invention relates to the measurements of oxygen saturations and concentrations of hemoglobins in arterial blood by using a pulse oximeter, and more particularly to the measurement of a concentration of carboxyhemoglobin.

2. Related art

A conventional pulse oximeter is constructed such that near-infrared rays of light and red rays of light are irradiated onto a living tissue, ratios of the pulsating components of attenuations of these lights having passed through the living tissue are processed, and an arterial oxygen saturation is noninvasively measured from the result of the computation.

The measuring principle of the pulse oximeter is known as disclosed in JP-A-53-26437, proposed by the applicant of the present patent application. The measuring principle of the pulse oximeter will be described in brief hereunder.

As shown in FIGS. 9(A) and 9(B), a living tissue R is divided into a blood layer R1 and a layer R2 of a tissue from which blood has removed (this tissue will be referred to as a pure tissue), and it is assumed that a thickness of the blood layer R1 is pulsated, but a thickness of the pure tissue layer R2 is not pulsated, viz., it is constant. Where the living tissue R is irradiated with light, an incident light amount IO is reduced by the living tissue R, and an amount of light passing through the living tissue R is I. When a thickness of the blood layer R1 is pulsated to be increased by $\Delta Db$, the amount of the transmitted light is reduced to be $(I-\Delta I)$. In this case, an attenuation $\Delta A$ of the light, which is produced by a thickness change $\Delta Db$ of the blood layer R1, is given by $$\Delta A = \log[I/(I-\Delta I)]$$

When lights of different wavelengths $\lambda 1$ and $\lambda 2$ are irradiated onto the living tissue R, a ratio $\Phi$ of attenuations $\Delta A1$ and $\Delta A2$ of lights of the wavelengths $\lambda 1$ and $\lambda 2$, which are produced by the pulsation of the tissue thickness is mathematically approximated by

[Expression 1]

$$\Phi = \Delta A1/\Delta A2 = \{\sqrt{]}(E1(E1+F))\}/[\sqrt{\{E2(E2+F)\}}] \quad (1)$$

This is theoretically and empirically confirmed.

In the above expression, E1,2(Ei) are absorption coefficients, F is a scattering coefficient of light in blood and has no wavelength dependency, and suffixes 2 represent the wavelengths $\lambda 1$ and $\lambda 2$. Assuming that light absorbing materials in blood are only oxyhemoglobin and deoxyhemoglobin, then the absorption coefficient Ei of the hemoglobin is given by the following expression.

$$Ei = SEOi + (1-S)Eri \quad (2)$$

In the expression, S is an oxygen saturation, and Eoi and Eri are an absorption coefficient Eoi of oxyhemoglobin and absorption coefficient Eri of deoxyhemoglobin. Substituting the expression (2) for the expression (1), then we have the following expression

[Expression 3]

$$\Phi = \Delta A1/\Delta A2 \quad (3)$$

$$= [\sqrt{\{[SEo1+(1-S)Er1]\{SEo1+(1-S)Er1+F)\}}]/$$
$$[\sqrt{\{(SEo2+(1-S)Er2)(SEo2+(1-S)Er2+F)\}}]$$

In the expression (3), Eo1, Er1, Eo2, Er2 and F are known values. Therefore, an oxygen saturation S can be obtained in a manner that $\Phi = \Delta A1/\Delta A_2$ is measured, substituted for the expression (3), and the expression is solved for the S.

The conventional pulse oximeter using two wavelengths of near-infrared rays of light and red rays of light cannot detect an increase of a concentration of carboxyhemoglobin COHb in blood. Accordingly, it has a disadvantage that an arterial oxygen saturation displayed is higher than an actual one. When the pulse oximeter is coupled to a patient suffering from carbon monoxide poisoning and operated for the monitoring, the result of the measurement by the pulse oximeter will lead to such misunderstanding by the medical staff that the sufficient amount of oxygen is present even though an amount of transporting oxygen is actually reduced. This is tremendously dangerous for the patient. In diagnosing a patient showing the carbon monoxide poisoning, it is very difficult to judge the illness as the carbon monoxide poisoning from only the symptoms of the patient. Accordingly, the carbon monoxide poisoning has frequently been missed in the diagnosis of the patient, though it is dangerous.

It is reported that in the operation under anesthesia, a patient shows the carbon monoxide poisoning in which a concentration of the carbon monoxide in blood reaches 10 to 30%. The cause of it is estimated that inhalative anesthetic and dried CO2 absorbent generate carbon monoxide. However, the conventional pulse oximeter cannot find the generated carbon monoxide. Accordingly, there is a danger of missing the generation of the carboxyhemogrobin.

Meanwhile, where the arterial blood pulsates, the theory teaches that concentration ratios of "n" number of light absorbing materials in the blood can be measured by using "n" number of wavelengths of lights. Accordingly, the theory also teaches that it is impossible to measure concentration ratios of three hemoglobins, oxyhemoglobin O2Hb, deoxyheoglobin RHband carboxyhemoglobin COHb by using two wavelengths of lights, and at least three wavelengths must be used for the measurement.

Actually, however, the influence by puretissues other than the blood will produce measuring errors. Accordingly, to accurately measure concentrations of "n" number of light absorbing materials in the blood, it is preferable to use (n+1) number of wavelengths. This fact was found and confirmed by us. The applicant of the present patent application developed an apparatus for determining concentrations of materials in blood based on the above fact, and filed the patent application on the apparatus (JP-B-5-88609). Other light absorbing materials, such as methemoglobin and bilirubin, are also contained in the blood. To remove the influence by those materials is attempted, the number of wavelengths used is further increased, and further cost to manufacture the apparatus is also increased.

In adding a third wavelength for measuring the carboxyhemoglobin COHb to the pulse oximeter (JP-A-5-228129), the absorption coefficients of it at the wavelengths of lights, which are longer than the red wavelengths, as shown in FIG. 10, are extremely small. Accordingly, it is very difficult to detect it. The absorption coefficient of the carboxyhemoglobin COHb at the wavelength of 700 nm is about 1/10 as large as that of oxyhemoglobin O2Hb. Accordingly, in this case, a change of the transmitted light which results from a change of the carboxyhemoglobin COHb, is about 1/10 as large as a change of the same which results from a change of the oxyhemoglobin O2Hb, and is extremely small. For this reason, where the third wavelength is selected from those wavelengths ranging from the red wavelengths to near-infrared wavelengths, a sensitivity of the apparatus is too small to discriminate the carboxyhemoglobin COHb from other hemoglobins Hb., and it is very difficult to measure the carboxyhemoglobin COHb.

Scharf proposed in his patent (U.S. Pat. No. 5,830,137) the use of the green wavelength region for the third wavelength. The absorption coefficient of every kind of hemoglobin, as shown in FIG. 10, is considerably large in the yellow and green wavelength regions. The absorption coefficients of the carboxyhemoglobin COHb and the oxyhemoglobin O2Hb in the wavelength region of 500 nm to 590 nm are at least 10 times as large as those at 660 nm. Light having passed through the blood is very weak, and the measurement at good S/N ratio is very difficult.

SUMMARY OF INVENTION

Accordingly, an object of the present invention is to provide an apparatus for determining concentrations of hemoglobins which, using an orange or orangey red wavelength region for the third wavelength in addition to the near-infrared and red wavelengths, which are conventionally used, can detect a change of the transmitted light by a change of the carboxyhemoglobin COHb at good S/N ratio, and can easily discriminate between the carboxyhemoglobin COHb and the deoxyhemoglobin RHb, and hence can perform a proper measurement of carboxyhemoglobin COHb.

Another object of the invention is to provide an apparatus for determining concentrations of hemoglobins, which includes a hemoglobin concentration indication system capable of indicating carboxyhemoglobin COHb concentrations measured by the apparatus as referred to in the major object, in a clinically effective, simple manner.

To achieve the above object, there is provided an apparatus for determining concentrations of hemoglobins comprising: a light source for emitting lights of at least three different wavelengths, a first wavelength in a near-infrared wavelength region of 790 to 1000 nm, a second wavelength in a red wavelength region of 640 to 675 nm, and a third wavelength in an orangy red wavelength region of 590 to 660 nm;

light receiving means for receiving lights that are emitted by the light source and transmitted through or reflected by a living tissue;

attenuation ratio processing means for processing attenuation ratios $\Phi$ on the wavelengths based on variations of signals associated with the wavelengths output from the light receiving means, which variations are caused by a pulsation of blood; and concentration ratio processing means for processing concentration ratios of at least oxyhemoglobin, deoxyhemoglobin and carboxyhemoglobin based on the output signals from the attenuation ratio processing means.

In the apparatus for determining concentrations of hemoglobins, the concentration ratio processing means processes concentration ratios of oxyhemoglobin, deoxyhemoglobin and carboxyhemoglobin on the assumption that an optimized linear relation is present between the concentrations of the hemoglobins and the attenuation ratios $\Phi$ output from the attenuation ratio processing means.

The apparatus further comprises oxygen saturation processing means for processing a functional oxygen saturation or a fractional arterial oxygen saturation based on an output signals of the concentration ratio processing means.

The apparatus further comprises alarm display means for displaying an alarm in accordance with a level of a concentration ratio of carboxyhemoglobin determined by the concentration ratio processing means.

The apparatus further comprises event input means for inputting events on the medical treatment on a patient when the events occur, and storing means for storing times and event information as input by the event input means, and the processing results output from the concentration ratio processing means.

The apparatus further comprises display means for displaying trends of the processing results, and the event information that is stored in the storing means.

The apparatus further comprises an interface used for transmitting the event information, the times and the processing results, which are stored in the storing means, to an external device.

According to another aspect of the invention, there is provided an apparatus for determining concentrations of hemoglobins comprising: a light source for emitting lights of different wavelengths; light receiving means for receiving lights that are emitted by the light source, transmitted through or reflected by a living tissue; value input means for inputting a concentration value of at least one kind of light absorbing material in blood for calibration; attenuation ratio processing means for processing attenuation ratios $\Phi$ on the wavelengths based on variations of signals associated with the wavelengths output from the light receiving means, which variations are caused by a pulsation of blood; and concentration processing means for processing concentrations of at least oxyhemoglobin, deoxyhemoglobin and carboxyhemoglobin based on the output signals from the attenuation ratio processing means and the concentration value of the in-blood material input by the value input means.

The apparatus further comprises storing means for storing data on attenuation ratio $\Phi$, and wherein the concentration processing means retrospectively processes over again at least one of oxyhemoglobin, deoxyhemoglobin and carboxyhemoglobin by using the data stored in the storing means and the in-blood material concentration value input to the value input means.

The apparatus for determining concentrations of hemoglobins comprises select means for giving an instruction to process a concentration ratio of carboxyhemoglobin.

When the select means does not give an instruction to process a concentration ratio of carboxyhemoglobin, the concentration ratio processing means processes concentration ratios of oxyhemoglobin and deoxyhemoglobin on the basis of variations of signals output from the light receiving means upon reception of lights of at least two different wavelengths that are emitted from the light source and transmitted through and reflected by a living tissue.

When the select means gives an instruction to process a concentration ratio of carboxyhemoglobin, the concentration ratio processing means processes concentration ratios of oxyhemoglobin, deoxyhemoglobin and carboxyhemoglobin on the basis of variations of signals output from the light receiving means upon reception of lights of at least three different wavelengths that are emitted from the light source, transmitted through or reflected by a living tissue.

According to yet another aspect of the invention, there is provided an apparatus for determining concentrations of hemoglobins comprising:

a light source for emitting lights of different wavelengths;

light receiving means for receiving lights that are emitted by the light source, transmitted through or reflected by a living tissue;

attenuation ratio processing means for processing attenuation ratios Φ on the wavelengths based on variations of signals associated with the wavelengths output from the light receiving means, which variations are caused by a pulsation of blood;

concentration ratio processing means for processing concentration ratios of at least oxyhemoglobin, deoxyhemoglobin and carboxyhemoglobin based on the output signals from the attenuation ratio processing means; and display means for displaying measured values of oxyhemoglobin, deoxyhemoglobin and carboxyhemoglobin on the X-Y coordinates.

In the apparatus, the light source for emitting lights of at least three different wavelengths, a first wavelength in a near-infrared wavelength region of 790 to 1000 nm, a second wavelength in a red wavelength region of 640 to 675 nm, and a third wavelength in an orangy red wavelength region of 590 to 660 nm.

BRIEF DESCRIPTION OF DRAWINGS

FIG. 1 is a block diagram showing a system arrangement of an apparatus for determining concentrations of hemoglobins, which is an embodiment of the present invention.

FIG. 2 is a diagram showing a display arrangement of a hemoglobin Hb concentration display unit in the FIG. 1 apparatus.

FIG. 3 is a diagram showing another display arrangement of the hemoglobin Hb concentration display unit in the FIG. 1 apparatus.

DETAILED DESCRIPTION OF PREFERRED EMBODIMENTS

Principle of the invention

Figure 7:
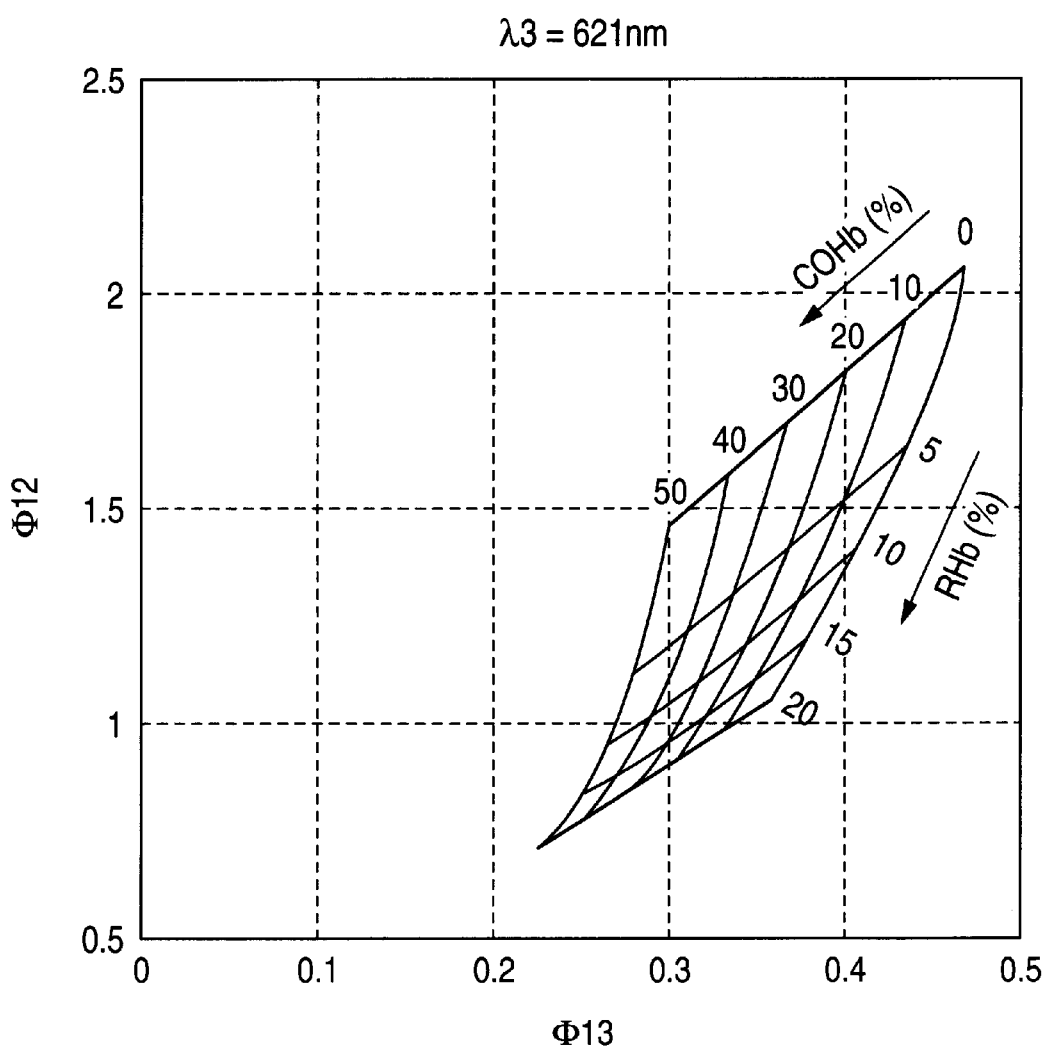
FIG. 7 is a graph showing characteristic curves describing relationships between two attenuation ratios Φ12 and Φ13 at the wavelengths of lights applied to the hemoglobin concentration determining apparatus.
Figure 8:
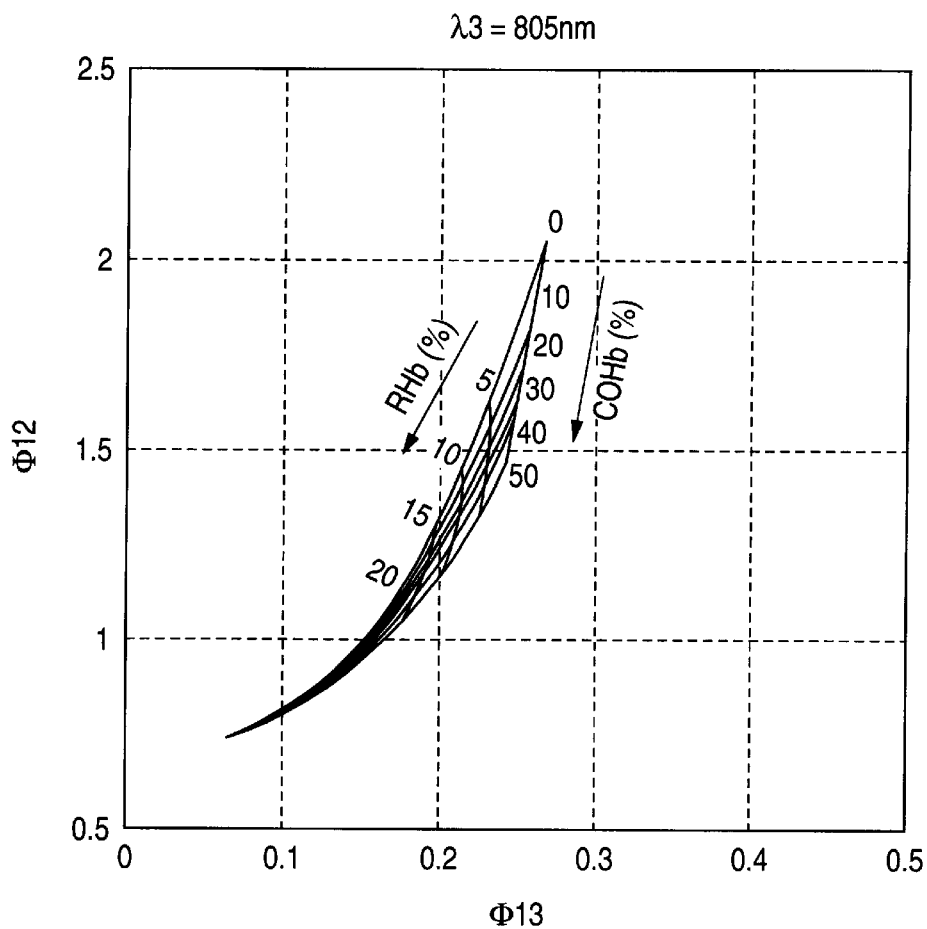
FIG. 8 is a graph showing characteristic curves describing relationships between two attenuation ratios Φ12 and Φ13 in the hemoglobin concentration determining apparatus when a third infrared wavelength of 805 nm is additionally used.
Figure 9:
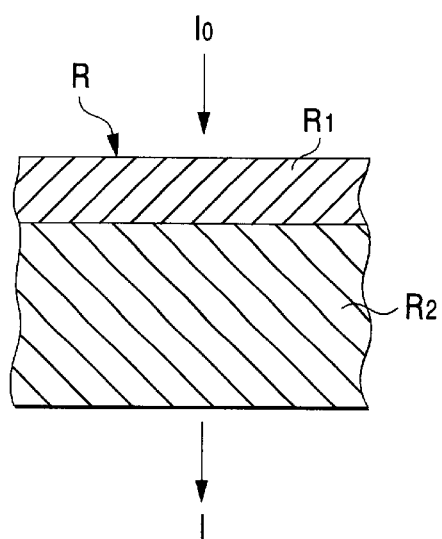
FIGS. 9(A) and 9(B) are cross sectional views showing a pulsation of a pure tissue layer, which pulsates with a blood layer.
Figure 9:
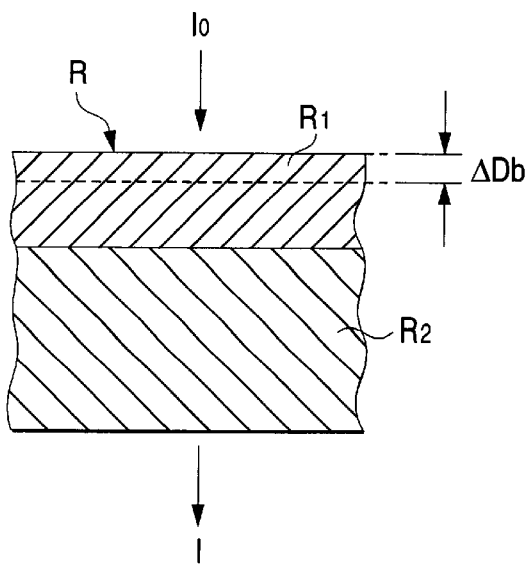
Figure 10:
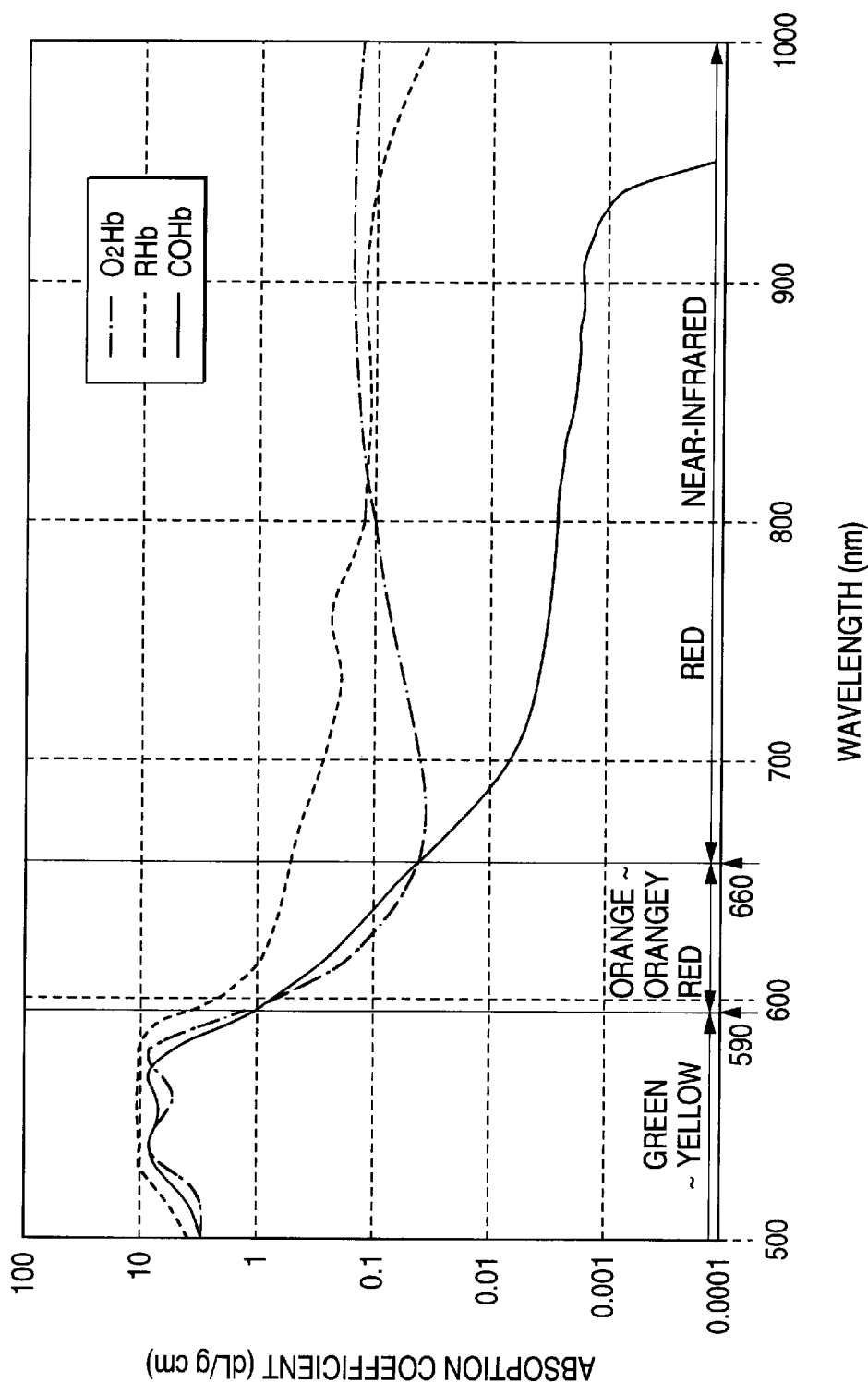
FIG. 10 is a graph showing a relationship between absorption coefficient and wavelengths, which are applied to the present invention.

The inventors of the present patent application discovered the following fact: when any of the orange or orangey red wavelengths is used for the third wavelength, in addition to the near-infrared and red wavelengths, which are conventionally used, a change of the transmitted light which results from a change of the carboxyhemoglobin COHb is detected at good S/N ratio, it is easy to discriminate between the carboxyhemoglobin COHb and the deoxyhemoglobin RHb, and hence it is possible to properly measure the carboxyhemoglobin COHb.

Where the near-infrared wavelength is 940 nm, the red wavelength is 660 nm, the near-infrared wavelength is 805 nm, and the orange wavelength is 621 nm, the values of the concentration ratios of deoxyhemoglobin RHb and carboxyhemoglobin COHb Φ12 and Φ32 were investigated. From the investigation, it was seen that at the infrared wavelength of 805 nm, the directions in which Φ12 and Φ32 change are coincident with each other for the changes of both the deoxyhemoglobin RHb and the carboxyhemoglobin COHb. In this state, it was found that it was difficult to discriminate between the deoxyhemoglobin RHb and the carboxyhemoglobin COHb as shown in FIG. 8. In the case of the orange wavelength of 621 nm, the orthogonality of a changing direction of the deoxyhemoglobin RHb and a changing direction of the carboxyhemoglobin COHb, increases. Accordingly, the discrimination is easy as shown in FIG. 7. This fact was found and confirmed.

COHb concentrations are conventionally expressed every 10% about acute carbon monoxide poisoning states (clinical symptoms) as in the following table (1).

TABLE 1

| COHb concentration (%) | Clinical symptoms |
| --- | --- |
| less than 10% | No obvious symptoms |
| 10–20 | frontal pain, headache, vasodilation of the skin |
| 20–30 | headache (pulsating), lack of vigor, emotional disturbance |
| 30–40 | splitting, confusion, vomiting, lack of strength, visual disorder |
| 40–50 | serious ataxia, hallucination, lack of strength, muscle weakness, hyperventilation, tachycardia |
| 50–60 | coma, convulsion, Cheyne-Stokes respiration, death sometimes |
| 60–70 | deep coma, weak breathing |
| more than 70% | respiratory standstill, circulatory collapse, death |

As seen from Table 1, the correspondence between the carboxyhemoglobin COHb concentration and the clinical symptoms will suffice for the clinical purposes, while not depending on precise expression of the COHb concentration (%) in steps of 1%. In an example of the concentration expression, acute carbon monoxide poisoning states may be expressed in two levels, "YES" and "NO", with the CORb concentration of 20% as a critical value, in another example of it, it may be expressed in three levels, "low concentration", "medium concentration" and "high concentration".

The preferred embodiment of an apparatus for determining concentrations of hemoglobins, which is constructed according to the present invention, will be described with reference to the accompanying drawings.

Embodiments

FIG. 1 is a block diagram showing a system arrangement of an apparatus for determining concentrations of hemoglobins constructed to the present invention. In FIG. 1, reference numerals 1, 2 and 3 indicate light emitting elements as light sources. Those elements 1, 2 and 3, respectively, emit near-infrared light of a first wavelength λ1, which is any of 790 nm to 100 nm, preferably 940 nm±5 nm, red light of a second wavelength λ2, which is any of 640 nm to 675 nm, preferably 660 nm±5 nm, and orangy red light of a third wavelength λ3, which is any of 590 nm to 660 nm, preferably 621 nm±5 nm. Those light emitting elements are driven by a drive circuit 4. The lights emitted from those elements 1, 2 and 3 transmit through a living tissue 5, and is received by a light receiving element 6 as light receiving means. The light receiving element 6 converts the lights into corresponding electrical signals. Those electrical signals are amplified by an amplifier 7, and applied to a multiplexer 8. The multiplexer then delivers respectively those signals to filters 9, 10 and 11, which are provided corresponding to the wavelengths of the lights.

Those filters 9 to 11 remove the high frequency components from those signals, and send the resultant signals to an A/D converter 12, which in turns converts those signals into digital signals. Then, the digital signals are input to a logarithm processing circuit 14, a Φ processing circuit 15 as attenuation ratio processing means for processing attenuation ratios Φ, and an Hb concentration processing circuit 16 as hemoglobin Hb concentration processing means. Reference numeral 13 indicates a timing control circuit 13. The timing control circuit sends necessary timing signals to the drive circuit 4, multiplexer 8 and A/D converter 12 to control the operations of those circuits.

The logarithm processing circuit 14 processes I1, I2, and I3 as the output signals of the A/D converter 12 to produce the logarithms lnI1, lnI2 and lnI3 of them. The Φ processing circuit 15 extracts the pulsating components from the logarithms lnI1, lnI2 and lnI3 obtained by the logarithm processing circuit 14, and processes Φ12=ΔlnI1/ΔlnI2 and Φ13=ΔlnI1/ΔlnI3. The Bb concentration processing circuit 16 solves simultaneous equations describing the ratios Φ, and obtains concentration ratios of oxyhemoglobin O2Hb, deoxyhemoglobin RHb and carboxyhemoglobin COHb.

The computation expression in the Hb concentration processing circuit 16 is as given by the following expression.

[Expression 4]

$$\Phi 12=\Delta A1/\Delta A2=[\surd\{(Eo1 \cdot O2Hb+$$
$$Er1 \cdot RHb+Ec1 \cdot COHb)(Eo1 \cdot O2Hb+Er1 \cdot RHb+Ec1 \cdot COHb$$
$$+F)\}]/[\surd\{(Eo2 \cdot O2Hb+Er2 \cdot RHb+Ec2 \cdot$$
$$COHb)(Eo2 \cdot O2Hb+Er2 \cdot RHb+Ec2 \cdot COHb+F)\}] \quad (4)$$

$$\Phi 13=\Delta A1/\Delta A3=[\surd\{(Eo1 \cdot O2Hb+$$
$$Er1 \cdot RHb+Ec1 \cdot COHb)(Eo1 \cdot O2Hb+Er1 \cdot RHb+Ec1 \cdot COHb$$
$$+F)\}]/[\surd\{(Eo3 \cdot O2Hb+Er3 \cdot RHb+Ec3 \cdot$$
$$COHb)(Eo3 \cdot O2Hb+Er3 \cdot RHb+Ec3 \cdot COHb+F)\}] \quad (4')$$

In the above expressions, RHb is a concentration ratio of the deoxyhemoglobin, O2Hb is a concentration ratio of oxyhemoglobin, and COHb is a concentration ratio of carboxyhemoglobin. Eoi (i=1,2,3) is an absorption coefficient of the oxyhemoglobin O2Hb. Eri (i=1,2,3) is an absorption coefficient of the deoxyhemoglobin RHb. Eci(i=1,2,3) is an absorption coefficient of the carboxyhemoglobin COHb. F is a scattering coefficient, i=1, 2, 3 represent wavelengths λ1, λ2, λ3. Those coefficients Eoi, Eri, Eci and F are known. Accordingly, the concentration ratios of the oxyhemoglobin O2Hb, the deoxyhemoglobin RHb and the carboxyhemoglobin COHb can be obtained in a manner that $\Phi 2=\Delta A1/\Delta A2$ and $\Phi 13=\Delta A1/\Delta A3$ are measured, the measured ones are substituted for the simultaneous equations, and those equations are solved.

While the concentration ratios of the oxyhemoglobin O2Hb, the deoxyhemoglobin RHb and the carboxyhemoglobin COHb are obtained from Φ12 and Φ32 by solving the simultaneous equations, the ratios may be obtained by referring to a table, which is prepared in advance by using computations or experiment results.

A concentration ratio of the carboxyhemoglobin COHb may also be obtained by using the following equations.

The blood is a light scattering material. Accordingly, an equation describing an actual relation between an attenuation and each concentration light absorbing materials in blood is non-linear. Practically, the equations may be handled as linear equations, however. For a non-light scattering material, Lambert-Beer's law is generally applicable for that relation, and the relation may be expressed by a linear equation, and expressed by the following equations. However, those equations cannot be applied to the blood having a light scattering nature directly.

[Expression 5]

$$\Phi 12=[(Eo1 \cdot O2Hb+Er1 \cdot RHb+Ec1 \cdot COHb)]/[(Eo2 \cdot O2Hb+Er2 \cdot RHb+Ec2 \cdot COHb)] \quad (5)$$

$$\Phi 13=[(Eo1 \cdot O2Hb+Er1 \cdot RHb+Ec1 \cdot COHb)]/[(Eo3 \cdot O2Hb+Er3 \cdot RHb+Ec3 \cdot COHb)] \quad (5')$$

The present invention newly presents the novel simplest computation expressions instead of the conventional computation expressions by Lambert-Beer, for example. To start, a population is set up, and blood is actually sampled from the population. Concentrations of various types of hemoglobins Hb are measured in a highly accurately measuring manner, for example, by using a CO— Oximeter. At this time, the pulsating waves are also measured, whereby attenuation ratios Φ are processed. The values of those measured hemoglobins Rb and the attenuation ratios Φ are substituted for the following equations.

[Expression 6]

$$\Phi 12=A12 \cdot O2Hb+B12 \cdot RHb+C12 \cdot COHb \quad (6)$$

$$\Phi 13=A13 \cdot O2Hb+B13 \cdot RHb+C13 \cdot COHb \quad (6')$$

Where a plural number of measurements are carried out for the population, the same number of the above equations ([Expression 6]) as that of the number of the measurements are prepared. The equations ([Expression 6]) contain a total of six unknown quantities, A12, B12, C12, A13, B13, and C13. Therefore, those unknown quantities may be obtained by using six equations. By substituting the thus processed unknown quantities for the equations ([Expression 6]), the concentration ratios of the hemoglobins Hb can be processed by using the attenuation ratios Φ measured.

If the population is increased and more than six number of computation expressions are set up, the coefficients satisfying all the expressions cannot be obtained. If the functions of those computation expressions are optimized and the coefficients are processed, the optimum coefficients in the population can be obtained. As the population becomes larger, the universality of the computation expressions increases. A process of optimizing the functions is as by the following expression 2n number of equations are obtained.

[Expression 7]

$$\Phi 12i=A12 \cdot O2Hbi+B12 \cdot RHbi+C12 \cdot COHbi \quad (7)$$

$$\Phi 13i=A13 \cdot O2Hbi+B13 \cdot RHbi+C13 \cdot COHbi \quad (7')$$

A process in which the square sum of a difference between a value Φ12ci obtained by processing the right sides of the linear equations (Equation 7) and an actually measured value Φ12mi is used as an objective function to be optimized, and is minimized, can be realized by using the following expression.

[Expression 8]

$$f = \Sigma(i=1\sim n)\{((\Phi 12ci - \Phi 12mi)^2$$
$$+ (\Phi 13ci - \Phi 13mi)^2\}$$
$$= \Sigma(i=1\sim n)\{(A12 \cdot O2Hbi + B12 \cdot RHbi +$$
$$C12 \cdot COHbi - \Phi 12mi)^2$$
$$+ (A13 \cdot O2Hbi + B13 \cdot RHbi + C13 \cdot COHbi - \Phi 13mi)^2$$
$$\} \tag{8}$$

The coefficients A12, B12, C12, A13, B13, and C13, which minimize f as the objective function of the equations ([Expression 8]) are obtained by using the steepest descent method or the like, whereby computation expressions may be determined.

In FIG. 1, signals representing concentration ratios of oxyhemoglobin O2Hb, deoxyhemoglobin RHb and carboxyhemoglobin COHb, which are processed by the above-mentioned processing process in the Hb concentration processing circuit 16, are input to an Hb concentration display unit 17 as hemoglobin Hb concentration display means, a trend display unit 18 as trend display means, a storage circuit 19 as storing means, and an alarm circuit 20 as alarm display means. In this case, the Hb concentration display unit 17, as shown in FIGS. 2 to 5, displays an arterial oxygen saturation SpO2 and a carboxyhemoglobin COHb concentration.

FIG. 2 exemplarily shows an arrangement of the Hb concentration display unit 17. In the display arranged as shown in FIG. 2, SpO2(%)=O2Hb/(O2Hb+RHb) (%) as a functional oxygen saturation or SpO2 (%)=O2Hb/(O2Hb+RHb+COBb)(%) as a fractional oxygen saturation is selected by a functional/fractional display select circuit 23 (see FIG. 1), and the selected one is displayed. Specifically, the display, as shown, contains an oxygen saturation SpO2 (%) numerical display section 30 and a COHb concentration (%) numerical display section 31. The display further contains a functional select switch/select status display section 34 and a fractional select switch/select status display section 35, which are provided in association with the oxygen saturation SpO2 (%) numerical display section 30. The "functional oxygen saturation" or "fractional oxygen saturation" is selected and the selected one is displayed by use of the related section 34 or 35.

A numerical value to be displayed in the oxygen saturation SpO2 (%) numerical display section 30 is the one processed using three wavelengths or two wavelengths of red and near-infrared lights as in the conventional case, which is selected by 3-wavelength/2-wavelength calculation display select circuit 24 (FIG. 1). in this case, to display the selected numerical value, a COHb measuring button 36 is used. When the COHb measuring button 36 is turned on, concentrations of various types of hemoglobins inclusive of carbon monoxide hemoglobin may be measured using three wavelengths. When it is turned off, an oxygen saturation (SpO2) may be measured as in the conventional manner using two wavelengths.

FIG. 3 shows another display arrangement of the Hb concentration display unit 17. In the display arranged as shown in FIG. 3, the fractional SpO2 (%) is displayed in the oxygen saturation SpO2 (%) numerical display section 30. The COHb concentration (%) is indicated in any of three dangerous levels by a dangerous level indicator 32. Two levels may be used in lieu of three levels, for the purpose of a dangerous indication of the COHb concentration. The remaining display arrangement is the same as that of the FIG. 2 one. No further description of it will be given here, while like portions are indicated by like reference numerals in FIG. 2.

Figure 4:
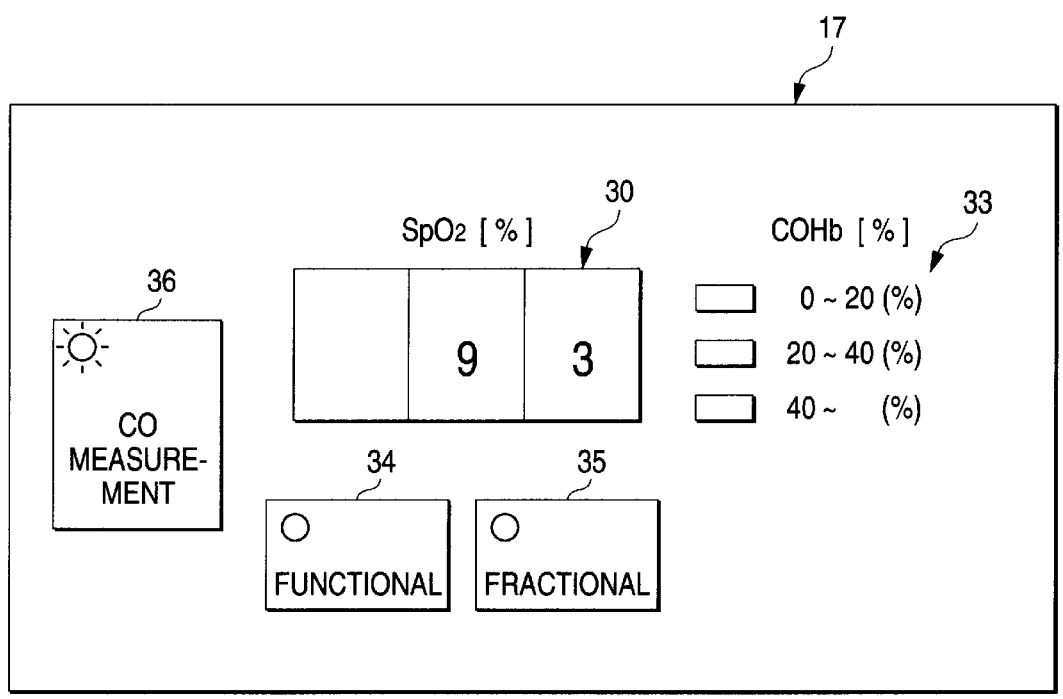
FIG. 4 is a diagram showing still another display arrangement of the hemoglobin Hb concentration display unit in the FIG. 1 apparatus.
Figure 5:
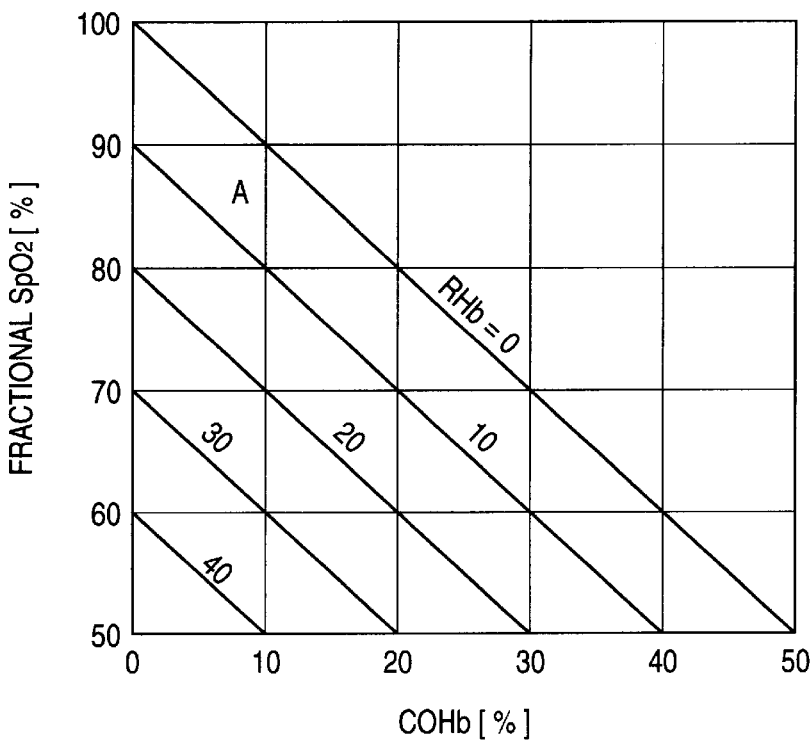
FIGS. 5(A) and 5(B) are diagrams showing additional display arrangements of the hemoglobin Hb concentration display unit in the FIG. 1 apparatus.
Figure 5:
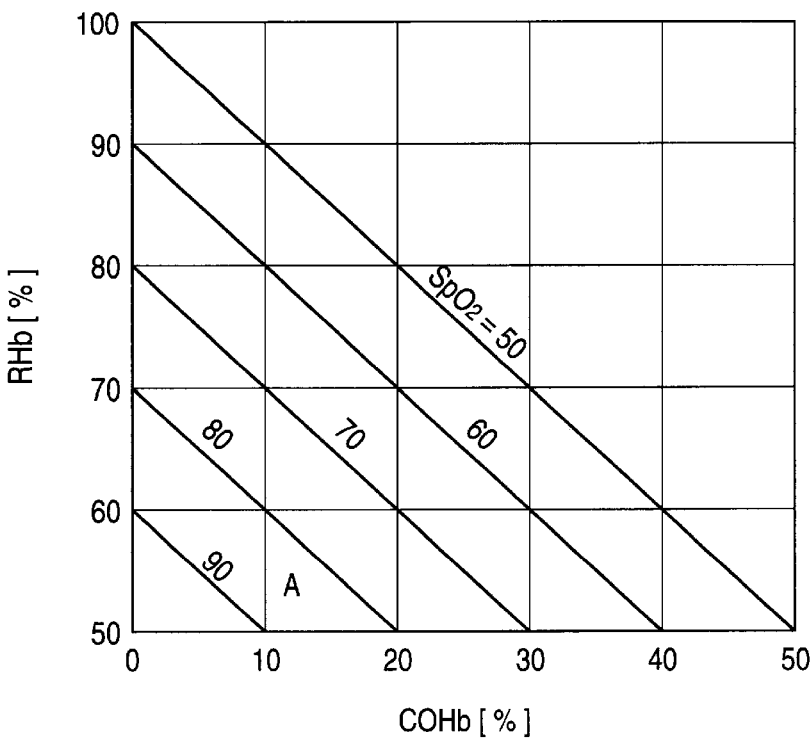

FIG. 4 shows yet another display arrangement of the Hb concentration display unit 17. In the display arranged as shown in FIG. 4, a dangerous level indicator 33 is used for indicating a dangerous level of the COHb concentration (%). In the dangerous level indicator 33, three dangerous levels shown in FIG. 3 are expressed in terms of numerical values. The remaining display arrangement is the same as of that the FIG. 2 one. No further description of it will be given here, while like portions are indicated by like reference numerals in FIG. 2.

A display of the Hb concentration display unit 17 may also be designed as shown in FIGS. 5(A) and 5(B). In the display of FIG. 5(A), the abscissa represents the carboxyhemoglobin concentration, the ordinate represents the fractional oxygen saturation (oxyhemoglobin concentration), and the oblique line represents the deoxyhemoglobin concentration. The display thus designed visually presents three kinds of concentrations at a time. In the FIG. 5(A) display, a point A indicates that the carboxyhemoglobin concentration is 10%, the fractional oxygen saturation (oxyhemoglobin concentration) is 85%, and the deoxyhemoglobin concentration is 5%. A display designed differently from the just-mentioned one is shown in FIG. 5(B). In this display, the abscissa represents the carboxyhemoglobin concentration, the ordinate represents the deoxyhemoglobin concentration, and the oblique line represents the fractional oxygen saturation (oxyhemoglobin concentration). The display also visually presents three kinds of concentrations at a time by use of the X-Y coordinates.

In FIG. 1, the alarm circuit 20 generates an alarm by light, sound, a message or the like when a concentration of carboxyhemoglobin COHb is higher than a value set by an alarm setting circuit 25. The alarm by light may be realized in the form of the lighting of an alarm lamp, the flickering of the lamp for indicating a dangerous level of the COHb concentration, the flickering of the COHb concentration (%) indicator or the like. The alarm by sound may be realized by an alarm sound representing the presence of COHb. In this case, the COHb concentration may be informed by varying the sound volume or the sound interval in accordance with its concentration. The sound volume or interval may be varied continuously in accordance with the concentration or intermittently in accordance with a dangerous level. Additionally, a sound synchronous with a pulsation may be changed in accordance with the COHb concentration. In this case, frequency of the sound or sounding duration may be changed in accordance with the presence of COHb. In FIG. 1, reference numeral 26 designates a clock circuit for clock operating the storage circuit 19.

Figure 6:
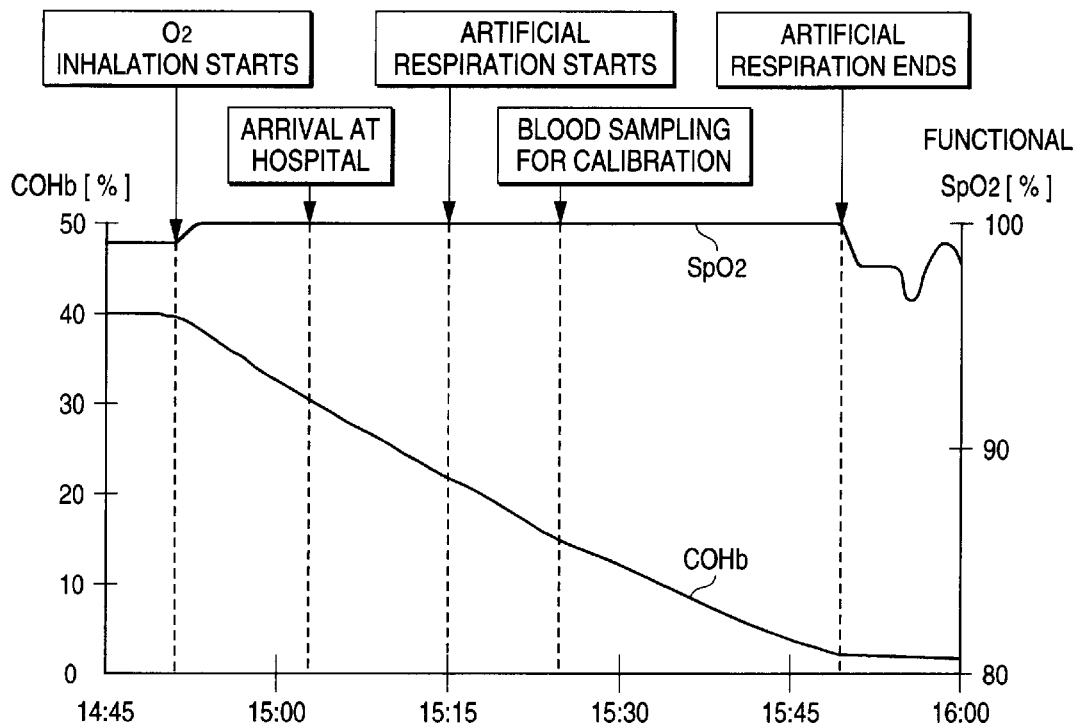
FIGS. 6(A) and 6(B) are diagrams showing different displays by a trend display unit shown in FIG. 1.
Figure 6:
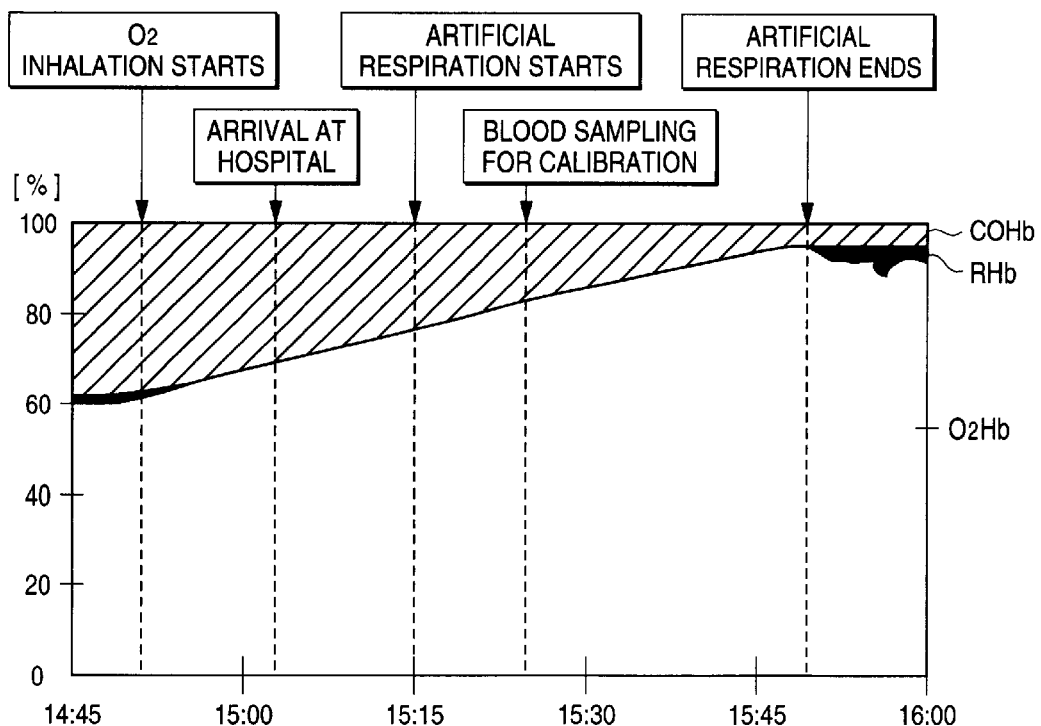

A further display of the trend display unit 18, which may be a liquid crystal display unit, is arranged as shown in FIGS. 6(A) and 6(B). The display visually presents trends of SpO2 (%) and COHb concentration (%). when events on the medical treatment applied to an acute carbon monoxide poisoning patient or the like occurs, information on the events is input to the hemoglobin concentration determining apparatus from an event input circuit 21 (FIG. 1), and displayed on the display screen of the trend display unit 18. The event information may be oxygen inhalation, arrival at hospital, blood sampling forcalibration, start of artificial respiration, and start of anesthesia or the like. The attenuation ratio Φ and the concentration ratios of oxyhemoglobin O2Hb, deoxyhemoglobin RHb and carboxyhemoglobin COHb, which are processed in the Hb concentration processing circuit 16, and the event information are transmitted to and stored in the storage circuit 19. Even after the power supply is interrupted or stopped, the data thus stored in the storage circuit 19 is retained, and is displayed by the trend display unit 18.

As show in FIG. 6(A), trends of the concentrations of the hemoglobins may be displayed for both the functional and the fractional oxygen saturations (SpO2). The concentrations of the oxyhemoglobin O2Hb, deoxyhemoglobin RHb and carboxyhemoglobin COHb may be displayed in terms of %, together with the event information (FIG. 6B). In the apparatus, the data that is stored in the storage circuit 19 may be sent to an external device, e.g., personal computer, through an external interface (FIG. 1).

The hemoglobin concentration determining apparatus shown in FIG. 1 includes a value input circuit for calibration 22 for inputting an in-blood light absorbing material concentration, which is measured by the blood sampling. The data from the value input circuit for calibration 22 is input to the Hb concentration processing circuit 16. The Hb concentration processing circuit 16 performs calibration computations on the oxyhemoglobin O2Hb, deoxyhemoglobin RHb and carboxyhemoglobin COHb. The calibration computation may be performed in the following way.

When a change of an attenuation by a pulsation of a living tissue, which is caused by a pulsation of blood is allowed for, a ratio Φ of the attenuations is expressed by (as described in JP-A-8-322822)
[Expression 9]

$$\Phi 12 = \Delta A1/\Delta A2$$

$$= [\sqrt{\{(Eo1 \cdot O2Hb+}$$

$$Er1 \cdot RHb + Ec1 \cdot COHb)(Eo1 \cdot O2Hb+$$

$$Er1 \cdot RHb + Ec1 \cdot CORb + F)\} - Ex]/[$$

$$\sqrt{\{(Eo2 \cdot O2Hb + Er2 \cdot RHb}$$

$$+Ec2 \cdot COHb)(Eo2 \cdot O2Hb + Er2 \cdot RHb + EC2 \cdot COHb$$

$$+F)\} - Ex] \tag{9}$$

$$\Phi 13 = \Delta A1/\Delta A3$$

$$= [\sqrt{\{(Eo1 \cdot O2Hb + Er1 \cdot RHb + Ec1 \cdot COHb)}$$

$$(Eo1 \cdot O2Hb+$$

$$Er1 \cdot RHb + Ec1 \cdot COHb + F)\} - Ex]/[\sqrt{\{}$$

$$(Eo3 \cdot O2Hb + Er3 \cdot RHb+$$

$$Ec3 \cdot COHb)(Eo3 \cdot O2Hb + Er3 \cdot RHb + Ec3 \cdot COHb$$

$$+F)\} - Ex] \tag{9'}$$

In the above equations, EX is a term indicating an attenuation caused by the pulsation of the pure tissue, and is unknown.

The unknown quantity EX may be determined by substituting the values obtained by sampling blood and measuring it for the above equations. Subsequently the simultaneous equations containing the thus determined unknown quantity EX are used, and highly accurate measurement results based on the pure tissue pulsation will be produced. Further, if the computation is carried out over again on the attenuation ratios Φ or the concentration rations of hemoglobins that are stored in the storage circuit 19 before the values for calibration are input by using the in-blood material concentration values obtained by sampling blood and measuring it, highly accurate measurement results can be obtained retrospectively.

Another calibration process will be described. The calibration process is applied for a calibration on an error caused by other light absorbing materials in blood, such as methemoglobin and bilirubin. A computation expression constructed while allowing for methemoglobin MeHb is given by
[Expression 10]

$$\Phi 12 = \Delta A1/\Delta A2$$

$$= [\sqrt{\{(Eo1 \cdot O2Hb + Er1}$$

$$\cdot RHb + Em1 \cdot MetHb + Ec1 \cdot COHb)(Eo1$$

$$\cdot O2Hb + Er1 \cdot RHb + Em1 \cdot MetHb + Ec1 \cdot COHb+$$

$$F)\} - Ex]/[\sqrt{\{(Eo2 \cdot O2Hb + Er2 \cdot RHb + Em2 \cdot MetHb + Ec2 \cdot}$$

$$COHb)(Eo2 \cdot O2Hb + Er2 \cdot RHb + Em2 \cdot MetHb + Ec2 \cdot COHb + F)\}$$

$$-Ex] \tag{10}$$

$$\Phi 13 = \Delta A1/\Delta A3$$

$$= [\sqrt{\{(Eo1 \cdot O2Hb + Em1 \cdot}$$

$$RHb + Em1 \cdot MetHb + Ec1 \cdot$$

$$COHb)(Eo1 \cdot O2Hb + Er1 \cdot RHb + Em1 \cdot MetHb$$

$$+Ec1 \cdot COHb + F)\} - Ex]/[\sqrt{\{(Eo3 \cdot O2Hb + Er3 \cdot RHb}$$

$$+Em3 \cdot MetHb + Ec3 \cdot COHb)(Eo3 \cdot O2Hb+$$

$$Er3 \cdot RHb + Em3 \cdot MetHb + Ec3 \cdot COHb$$

$$+F)\} - Ex] \tag{10'}$$

The unknown quantity EX may be processed by substituting measured hemoglobins O2Hb, RHb, COHb, and MetHb for the above equations. Further, the concentration ratios of the hemoglobins O2Hb, RHb and COHb may be obtained by substituting the processed unknown quantity EX and the methemoglobin MetHb measured by the blood sampling method for the equations, and solving the simultaneous equations on the assumption that EX and MetHb are constant. Incidentally, in an alternative computation, terms of bilirubin are incorporated into the above equations, and a bilirubin value measured by the blood sampling method is substituted for the equations. The same thing is valid for any of other in-blood light absorbing materials.

While the preferred embodiment of the invention has specifically be described, it should be understood that the present invention is not limited to the embodiment mentioned above, but may variously be modified, altered and changed within true spirits of the invention.

As seen from the foregoing description, an apparatus for determining concentrations of hemoglobins comprises: a light source for emitting lights of at least three different wavelengths, a first wavelength in a near-infrared wavelength region of 790 to 1000 nm,, a second wavelength in a red wavelength region of 640 to 675 nm, and a third wavelength in an orangy red wavelength region of 590 to 660 nm; light receiving means for receiving lights that are emitted by the light source and transmitted through or reflected by a living tissue; attenuation ratio processing means for processing an attenuation ratio Φ on the wavelengths based on variations of signals associated with the wavelengths output from the light receiving means, which variations are caused by a pulsation of blood; and concentration ratio processing means for processing concentration ratios of at least oxyhemoglobin, deoxyhemoglobin and carboxyhemoglobin based on the output signals from the attenuation ratio processing means. Accordingly, the apparatus can detect a change of the transmitted light by a change of the carboxyhemoglobin COHb at good S/N ratio, and can easily discriminate between the carboxyhemoglobin COHb and the deoxyhemoglobin RHb, and hence can perform a proper measurement of carboxyhemoglobin COHb.

Where the hemoglobin concentration determining apparatus is used, in measuring SpO2 when COHb is not present in blood, the measurement using two wavelengths is better than that using three wavelengths in the measuring accuracy since the former is based on the data accumulated for a long time. To diagnose a patient not suffering from carbon monoxide poisoning, the COHb measuring button 36 is turned off, the apparatus highly accurately measures an oxygen saturation (SpO2) by using two wavelengths as in the conventional case. To diagnose a patient who may suffer from carbon monoxide poisoning, the COHb measuring button 36 is turned on, the apparatus measures concentrations of various types of hemoglobins including carboxyhemoglobin by using three wavelengths. A simple display of presence or absence of carbon monoxide or a dangerous level, not a precise display of a carbon monoxide concentration in steps of 1%, will be very useful when an ambulance man decides if the patient is to be transported to a hospital installed with hyperbaric oxygen therapy, or when the medical staff decides how the medical treatment progresses. Further, when a concentration of a light absorbing material in blood, measured by the blood sampling method, is used as a calibrated value, a concentration of each hemoglobin can be measured more accurately.

The best method of measuring a concentration of carboxyhemoglobin COHb in blood is a method of measuring the same by the blood sampling method using the CO-oximeter. When highly reliable, measured values obtained by such a method are further calibrated, the accuracy of the measured values is further increased. It is a common practice that oxygen inhalation is used for the treatment of the patient suffering from the acute carbon monoxide poisoning. In such a treatment, the apparatus of the invention enables one to highly reliably monitor a process in which the concentration of carboxyhemoglobin COHb progressively decreases.

When the apparatus for determining concentrations of hemoglobins is used, the concentrations of three hemoglobins, i.e., carboxyhemoglobin concentration, deoxyhemoglobin concentration and fractional oxygen saturation (oxyhemoglobin concentration), are displayed on the X-Y coordinates, and hence one can visually grasp those concentrations at a time.

In the apparatus, a change of each hemoglobin concentration with time may be checked together with an event marker or the like concerning the treatment for the patient. The data obtained is very useful in mapping out the course of treatment. Further, the effects of the treatment can visually be checked.

With the event information on a trend graph provided by the storing functions and event marker functions , the subsequent medical treatment of a patient of acute carbonate monoxide poisoning who has been transported into a hospital is made easy. When the patient resprirates the air spontaneously, a period that the quantity of carboxyhemoglobin COHb is reduced to half quantity is about 4 hours. It is about 80 minutes by the oxygen inhalation, and is about 14 minutes by the positive pressure ventilation by oxygen. It is vital to rapidly reduce the carboxyhemoglobin concentration in blood by the oxygen inhalation. The function of storing and reproducing a change of the in-blood hemoglobin Hb concentration of the patient for a period from a time that a patient of carbon monoxide poisoning is found till he is transported to the hospital, and the history of oxygen inhalation, provides important data in mapping out the course of medical treatment.

What is claimed is:

1. An apparatus for determining concentrations of hemoglobins comprising:

a light source for emitting lights of at least three different wavelengths, a first wavelength in a near-infrared wavelength region of 790 to 100 nm, a second wavelength in a red wavelength region of 640 to 675 nm, and a third wavelength in an orangy red wavelength region of 590 to 660 nm;

light receiving means for receiving light emitted by said light source, transmitted through a living tissue or reflected by the living tissue;

attenuation ratio processing means for processing attenuation ratios on said wavelengths based on variations of signals associated with said wavelengths output from said light receiving means, said variations are caused by a pulsation of blood; and concentration ratio processing means for processing concentration ratios of at least oxyhemoglobin, deoxyhemoglobin and carboxyhemoglobin based on the output signals from said attenuation ratio processing means.

2. An apparatus for determining concentrations of hemoglobins according to claim 1, wherein said concentration ratio processing means processes concentration ratios of oxyhemoglobin, deoxyhemoglobin and carboxyhemoglobin on the assumption that an optimized linear relation is present between the concentrations of said hemoglobins and the attenuation ratios Φ output from said attenuation ratio processing means.

3. An apparatus for determining concentrations of hemoglobins comprising;

a light source for emitting lights of different wavelengths;

light receiving means for receiving light emitted by said light source, transmitted through a living tissue or reflected by the living tissue;

attenuation ratio processing means for processing attenuation ratios on said wavelengths based on variations of signals associated with said wavelengths output from said light receiving means, said variations caused by a pulsation of blood;

concentration ratio processing means for processing concentration ratios of at least oxyhemoglobin, deoxyhemoglobin and carboxyhemoglobin based on the output signals from said attenuation ratio processing means; and oxygen saturation processing means for processing one of a functional oxygen saturation and a fractional arterial oxygen saturation based on an output signals of said concentration ratio processing means.

4. An apparatus for determining concentrations of hemoglobins comprising:

a light source for emitting lights of different wavelengths;

light receiving means for receiving light emitted by said light source , transmitted through a living tissue or reflected by a living tissue;

attenuation ratio processing means for processing attenuation ratios on said wavelengths based on variations of signals associated with said wavelengths output from said light receiving means, said variations caused by a pulsation of blood;

concentration ratio processing means for processing concentration ratios of at least oxyhemoglobin, deoxyhemoglobin and carboxyhemoglobin based on the output signals from said attenuation ratio processing means; and alarm display means for displaying an alarm in accordance with a level of a concentration ratio of carboxyhemoglobin produced from said concentration ratio processing means.

5. An apparatus for determining concentrations of hemoglobins comprising:

a light source for emitting lights of different wavelengths;

light receiving means for receiving light emitted by said light source, transmitted through a living tissue or reflected by the living tissue;

attenuation ratio processing means for processing attenuation ratios on said wavelengths based on variations of signals associated with said wavelengths output from said light receiving means, said variations caused by a pulsation of blood;

concentration ratio processing means for processing concentration ratios of at least oxyhemoglobin, deoxyhemoglobin and carboxyhemoglobin based on the output signals from said attenuation ratio processing means;

event input means for inputting events on the medical treatment on a patient when said events occur; and storing means for storing times and event information as input by said event input means, and the processing results output from said concentration ratio processing means.

6. An apparatus for determining concentrations of hemoglobins according to claim 5, further comprising:

display means for displaying trends of said processing results, and said event information that is stored in said storing means.

7. An apparatus for determining concentrations of hemoglobins according to claim 5, further comprising:

an interface used for transmitting said event information, said times and said processing results, which are stored in said storing means, to an external device.

8. An apparatus for determining concentrations of hemoglobins comprising:

a light source for emitting lights of different wavelengths;

light receiving means for receiving light emitted by said light source, transmitted through the living tissue or reflected by the living tissue;

value input means for inputting a concentration value of at least one kind of light absorbing material in blood for calibration;

attenuation ratio processing means for processing attenuation ratios on said wavelengths based on variations of signals associated with said wavelengths output from said light receiving means, the variations caused by a pulsation of blood; and concentration processing means for processing concentrations of at least oxyhemoglobin, deoxyhemoglobin and carboxyhemoglobin based on the output signals from said attenuation ratio processing means and said concentration value of said in-blood material input by said value input means.

9. An apparatus for determining concentrations of hemoglobins according to claim 8, further comprising:

storing means for storing data on attenuation ratio, wherein said concentration processing means retrospectively processes over again at least one of oxyhemoglobin, deoxyhemoglobin and carboxyhemoglobin by using said data stored in said storing means and said in-blood material concentration value input to said value input means.

10. An apparatus for determining concentrations of hemoglobins comprising:

a light source for emitting lights of different wavelengths;

light receiving means for receiving light emitted by said light source, transmitted through or reflected by a living tissue;

attenuation ratio processing means for processing attenuation ratios on said wavelengths based on variations of signals associated with said wavelengths output from said light receiving means, which variations are caused by a pulsation of blood;

concentration ratio processing means for processing concentration ratios of at least oxyhemoglobin, deoxyhemoglobin and carboxyhemoglobin based on the output signals from said attenuation ratio processing means; and select means for giving an instruction to process a concentration ratio of carboxyhemoglobin;

wherein when said select means does not give an instruction to process a concentration ratio of carboxyhemoglobin, said concentration ratio processing means processes concentration ratios of oxyhemoglobin and deboxyhemoglobin on the basis of variations of signals output from said light receiving means upon reception of lights of at least two different wavelengths that are emitted from said light source and transmitted through and reflected by a living tissue, and when said select means gives an instruction to process a concentration ratio of carboxyhemoglobin, said concentration ratio processing means processes concentration ratios of oxyhemoglobin, deoxyhemoglobin and carboxyhemoglobin on the basis of variations of signals output from said light receiving means upon reception of lights of at least three different wavelengths that are emitted from said light source and transmitted through and reflected by a living tissue.

11. An apparatus for determining concentrations of hemoglobins comprising:

a light source for emitting lights of different wavelengths;

light receiving means for receiving light emitted by said light source, transmitted through a living tissue or reflected by the living tissue;

attenuation ratio processing means for processing attenuation ratios on said wavelengths based on variations of signals associated with said wavelengths output from said light receiving means, said variations caused by a pulsation of blood;

concentration ratio processing means for processing concentration ratios of at least oxyhemoglobin, deoxyhemoglobin and carboxyhemoglobin based on the output signals from said attenuation ratio processing means; and display means for displaying measured values of oxyhemoglobin, deoxyhemoglobin and carboxyhemoglobin on the X-Y coordinates.

12. An apparatus for determining concentrations of hemoglobins according to claim 3, wherein said light source for emitting lights of at least three different wavelengths, a first wavelength in a near-infrared wavelength region of 790 to 1000 nm, a second wavelength in a red wavelength region of 640 to 675 nm, and a third wavelength in an orangy red wavelength region of 590 to 660 nm.

13. An apparatus for determining concentrations of hemoglobins according to claim 4, wherein said light source for emitting lights of at least three different wavelengths, a first wavelength in a near-infrared wavelength region of 790 to 1000 nm, a second wavelength in a red wavelength region of 640 to 675 nm, and a third wavelength in an orangy red wavelength region of 590 to 660 nm.

14. An apparatus for determining concentrations of hemoglobins according to claim 5, wherein said light source for emitting lights of at least three different wavelengths, a first wavelength in a near-infrared wavelength region of 790 to 1000 nm, a second wavelength in a red wavelength region of 640 to 675 nm, and a third wavelength in an orangy red wavelength region of 590 to 660 nm.

15. An apparatus for determining concentrations of hemoglobins according to claim 8, wherein said light source for emitting lights of at least three different wavelengths, a first wavelength in a near-infrared wavelength region of 790 to 1000 nm, a second wavelength in a red wavelength region of 640 to 675 nm, and a third wavelength in an orangy red wavelength region of 590 to 660 nm.

16. An apparatus for determining concentrations of hemoglobins according to claim 10, wherein said light source for emitting lights of at least three different wavelengths, a first wavelength in a near-infrared wavelength region of 790 to 1000 nm, a second wavelength in a red wavelength region of 640 to 675 nm, and a third wavelength in an orangy red wavelength region of 590 to 660 nm.

17. An apparatus for determining concentrations of hemoglobins according to claim 11, wherein said light source for emitting lights of at least three different wavelengths, a first wavelength in a near-infrared wavelength region of 790 to 1000 nm, a second wavelength in a red wavelength region of 640 to 675 nm, and a third wavelength in an orangy red wavelength region of 590 to 660 nm.

* * * * *

UNITED STATES PATENT AND TRADEMARK OFFICE
CERTIFICATE OF CORRECTION

PATENT NO.   : 6,415,236 B2
DATED        : July 2, 2002
INVENTOR(S)  : Naoki Kobayashi et al.

It is certified that error appears in the above-identified patent and that said Letters Patent is hereby corrected as shown below:

<u>Column 14,</u>
Line 18, please delete "100nm" and insert -- 1000nm --.

Signed and Sealed this

Tenth Day of February, 2004

JON W. DUDAS
*Acting Director of the United States Patent and Trademark Office*